(12) United States Patent
Rodrigues et al.

(10) Patent No.: US 9,618,633 B2
(45) Date of Patent: Apr. 11, 2017

(54) SIDE-ELECTRODES FOR A FARADAY CAGE ON A PHOTON-COUNTING DETECTOR ARRAY

(71) Applicant: TOSHIBA MEDICAL SYSTEMS CORPORATION, Otawara-shi (JP)

(72) Inventors: Miesher Lage Rodrigues, Buffalo Grove, IL (US); Gin Chung Wang, Lincolnshire, IL (US); Hao Yang, Vernon Hills, IL (US); Liang Cai, Arlington Heights, IL (US); Alan Karr, Port Barrington, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 150 days.

(21) Appl. No.: 14/692,519

(22) Filed: Apr. 21, 2015

(65) Prior Publication Data

US 2016/0313454 A1  Oct. 27, 2016

(51) Int. Cl.
*G01T 1/24* (2006.01)
*G01N 23/04* (2006.01)

(52) U.S. Cl.
CPC .......... *G01T 1/241* (2013.01); *G01N 23/046* (2013.01); *G01T 1/247* (2013.01); *G01N 2223/50* (2013.01)

(58) Field of Classification Search
CPC .. G01T 1/20; G01T 1/24; G01T 1/241; G01T 1/247; G01N 23/04; G01N 23/046; A61B 6/03; A61B 6/032; A61B 6/06; A61B 6/42; A61B 6/4208; A61B 6/4241; A61B 6/4266
See application file for complete search history.

(56) References Cited

U.S. PATENT DOCUMENTS

| 9,198,632 B2 | 12/2015 | Zhang et al. | |
| 2013/0251097 A1* | 9/2013 | Zou | A61B 6/032 378/9 |
| 2014/0319635 A1* | 10/2014 | Li | G01T 1/366 257/429 |
| 2016/0018537 A1* | 1/2016 | Zhang | G01T 1/247 250/371 |

FOREIGN PATENT DOCUMENTS

JP   2014-168688   9/2014

* cited by examiner

*Primary Examiner* — David E Smith
(74) *Attorney, Agent, or Firm* — Oblon, McClelland, Maier & Neustadt, L.L.P.

(57) ABSTRACT

A computed tomography (CT) detector apparatus includes a plurality of detectors arranged in a ring, each detector being arranged inside a Faraday cage having a plurality of voltage-biased side-electrodes arranged on a side surface of the Faraday cage. The detectors include photon-counting detectors (PCDs). A voltage applied to the voltage-biased side-electrodes decreases from the anode side of the PCD to the cathode side of the PCD.

20 Claims, 12 Drawing Sheets

SIDE-ELECTRODES FOR A FARADAY CAGE ON A PHOTON-COUNTING DETECTOR ARRAY

FIELD

Embodiments disclosed herein generally relate to detectors and computer tomography imaging system.

BACKGROUND

In most computer tomography (CT) scanners, the X-ray beam is polychromatic. Third-generation CT scanners generate images based upon data according to the energy integrated nature of the detectors. These conventional detectors are called energy-integrating detectors and acquire energy integrated X-ray data. On the other hand, photon-counting detectors are configured to acquire the spectral nature of the X-ray source, rather than the energy integrated nature. To obtain the spectral nature of the transmitted X-ray data, the photon-counting detectors split the X-ray beam into the X-ray beam's component energies or spectrum bins, and count a number of photons in each of the bins. The use of the spectral nature of the X-ray source in CT is often referred to as spectral CT. Since spectral CT involves the detection of the transmitted X-ray at two or more energy levels, spectral CT generally includes dual-energy CT by definition.

Photon-counting detectors in CT imaging systems are often produced from semiconductor materials such as Cadmium Zinc Telluride (CdZnTe), often referred to as CZT, Cadmium Telluride (CdTe), and Silicon (Si), among others. Semiconductor radiation detectors, e.g., CdZnTe, HgI2, and TlBr, have ideal characteristics to be used as imaging detecting devices: high effective atomic number ($Z_{eff}$) and high density ($\rho$). These characteristics provide a high probability for photoelectric absorption of incoming radiation photons, i.e., X-rays, thereby providing a high level of intrinsic detection efficiency. For example, the probability of the photoelectric effect occurring is measured by the cross section of interaction $\sigma$ given by $$\sigma \propto \frac{Z_{eff}^n}{E^3}$$

where n is a number that varies between 4 and 5. These characteristics are especially important when the physical size of the imaging detecting devices (detectors) needs to be reduced while maintaining the required detection efficiency.

Using sparse fourth-generation photon-counting detectors combined with third-generation detectors is a viable solution for future hybrid spectroscopic CT systems. This configuration requires the fourth-generation photon-counting detectors to be manufactured in a slender geometry, having one-dimensional arrays of detectors with segmented anodes in the slice direction. In this scenario, it may be required to maximize the intrinsic detection efficiency while reducing the overall dimensions of the fourth-generation photon-counting detectors (PCDs) in order to minimize the effective shadow on the third-generation detectors.

Figure 12:
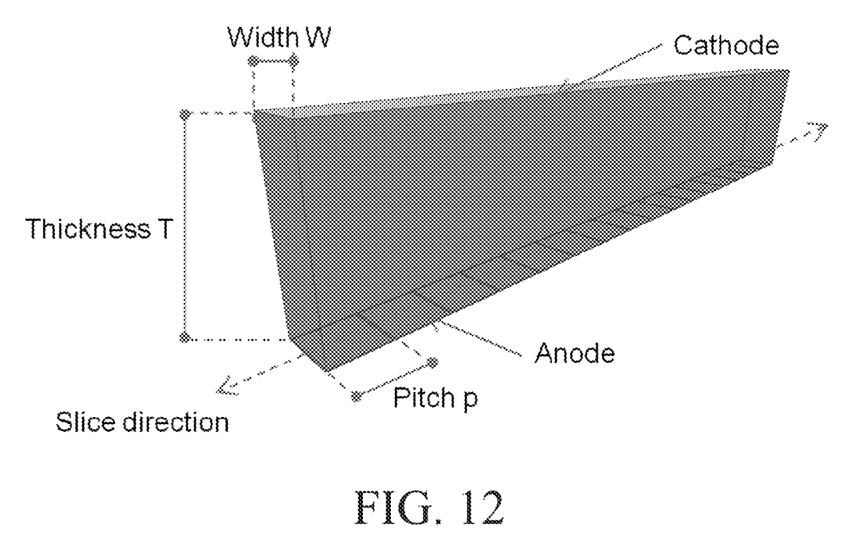
FIG. 12 illustrates a 1D 16-pixel imaging detector device having a slender geometry.
Figure 13:
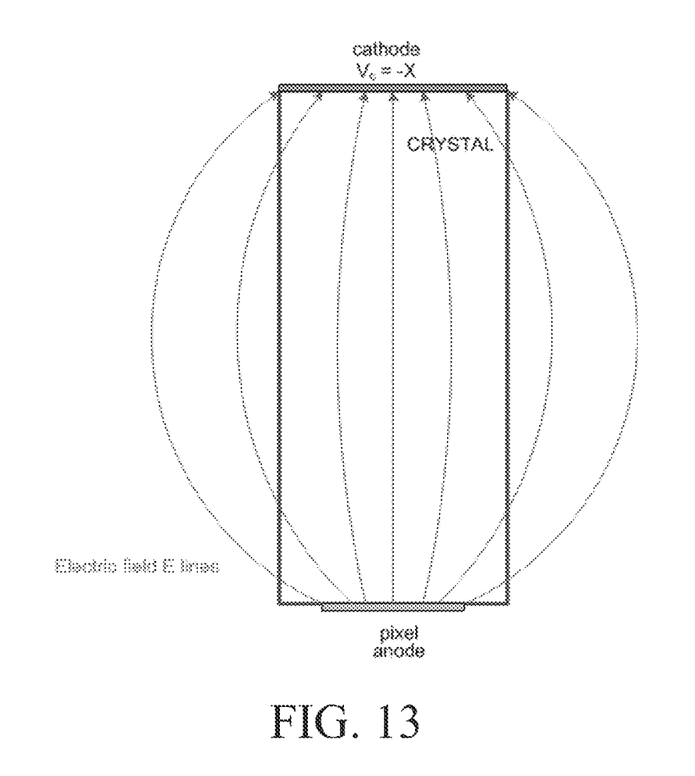
FIG. 13 illustrates charge losses near the surface of a semiconductor due to deformation of the operating electric field.

As shown in FIG. 12, the intrinsic detection efficiency can be maximized by increasing the thickness T while reducing the width W in order to minimize the effect of shadows onto the third-generation detectors. This would require semiconductor radiation detectors having a slender geometry having very small widths W (<2 mm). However, the slender shape of the detectors (small radiation detector widths W<2 mm) can cause severe deformation of the operating electric field near the lateral surfaces of the detector. As shown in FIG. 13, deformation of the operating electric field causes charge losses near the surface of the semiconductor, degrading the energy resolution of the detector. Moreover, charge loss at the surface of radiation detectors is worse for small detector widths due to the dipole effect.

Direct-conversion photon-counting detectors (PCDs) are sensitive to light and have to operate in a light-sealed environment. Furthermore, PCD systems that include ASICs to control the PCDs are sensitive to electromagnetic interference, and need to be operated inside a Faraday cage. The Faraday cage serves both as an electromagnetic shield and a light shield. However, the Faraday cage, which is biased at certain electrical potentials, can alter the operating electrical potential of the PCDs.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

In one embodiment, there is provided a computed tomography (CT), comprising: a plurality of detectors, each detector being arranged inside a Faraday cage having a plurality of voltage-biased side electrodes arranged on a side surface of the Faraday cage.

Figure 1:
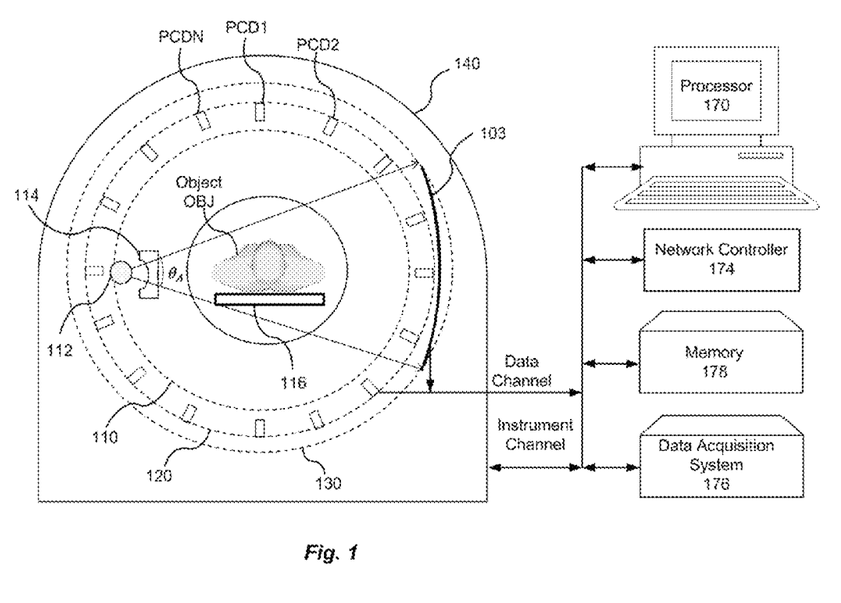
FIG. 1 illustrates a schematic diagram of an implementation of an image reconstruction apparatus having a coupled-ring topology.
Figure 2:
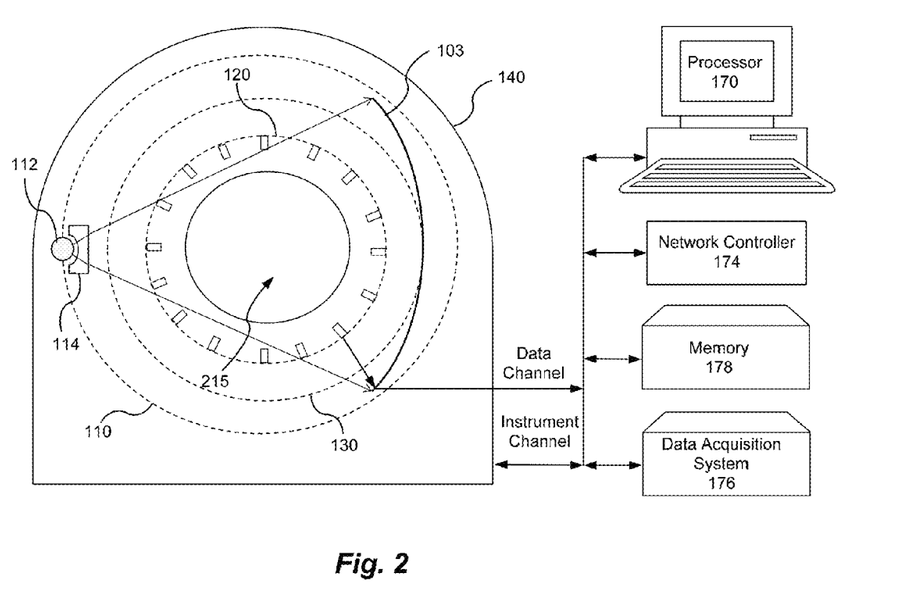
FIG. 2 illustrates a schematic diagram of an implementation of an image reconstruction apparatus having an inner-ring topology.

FIG. 1 and FIG. 2 show schematic views of CT scanner systems with hybrid systems having energy-integrating detectors arranged in a third-generation geometry and photon-counting detectors (PCDs) arranged in a fourth-generation geometry. FIG. 1 shows a coupled-ring topology with the X-ray source 112 inside the ring of PCDs and the X-ray detector unit 103 outside the ring of PCDs. In contrast, FIG. 2 shows an inner-ring topology with both the X-ray source 112 and the X-ray detector unit 103 outside the ring of PCDs.

Illustrated in FIG. 1 is an implementation for placing the PCDs in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector unit 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy-integrating detectors in the X-ray detector unit 103.

Also shown in FIG. 1 is circuitry and hardware for acquiring, storing, processing, and distributing X-ray projection data. The circuitry and hardware include: a processor 170, a network controller 174, a memory 178, and a data acquisition system 176.

In one implementation, the X-ray source 112 and the collimator/filter 114 are fixedly connected to a rotational component 110 that is rotatably connected to a gantry 140. The X-ray detector is similarly fixedly connected to a rotational component 130 that is rotatably connected to the gantry 140, while the PCDs are fixedly connected to a circular component 120 that is fixedly connected to the gantry 140. The gantry 140 houses many pieces of the CT scanner.

The gantry of the CT scanner also includes an open aperture 215 (shown in FIG. 2) enabling the object OBJ that is arranged on a table 116 positioned in a projection plane of the X-rays traveling from the X-ray source to the PCDs and detector unit 203. The "projection plane" is a volume wherein X-rays pass from the X-ray source 112 to the detectors including the PCDs and the detector unit 103. The "object space" is the intersection of the projection plane and the open aperture 215 of the gantry. The "image space" includes the union of projection planes corresponding to all projection angles of the X-ray source 112 as the X-ray source 112 rotates around the aperture of the gantry. The image space is generally larger than the object space enabling image reconstruction for a volume extending beyond the dimension of the object.

A scan is performed when an object OBJ occupies the object space and the X-ray source is rotated through a series of projection angles with the CT scanner acquiring projection data of the X-ray transmission/attenuation through the object OBJ at each projection angle.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1 includes a detector unit 103 having energy-integrating detectors arranged in a conventional third-generation geometry. The detector elements in the detector unit 103 can be more densely placed along the detector unit surface than the photon-counting detectors.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow-tie filter), and the detector unit 103 rotate around the object OBJ while the photon-counting detectors PCD1 through PCDN are stationary with respect to the object OBJ. In one implementation, the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 is mounted at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the X-ray source 112 optionally travels a helical path relative to the object OBJ, wherein the table 116 moves the object OBJ linearly in a predetermined direction perpendicular to the rotational plane of the rotational portion 110 as the rotational portion 110 rotates the X-ray source 112 and detector unit 103 in the rotational plane.

The motion of the rotational portion 110 around the object OBJ is controlled by a motion control system. The motion control system can be integrated with a data acquisition system or can be separate providing one way information regarding the angular position of the rotational portion 110 and the linear position of the table 116. The motion control system can include position encoders and feedback to control the position of the rotational portion 110 and the table 116. The motion control system can be an open loop system, a closed loop system, or a combination of an open loop system and a closed loop system. The motion control system can use linear and rotary encoders to provide feedback related to the position of the rotational portion 110 and the position of the table 116. The motion control system can use actuators to drive the motion of the rotational portion 110 and the motion of the table 116. These positioners and actuators can include: stepper motors, DC motors, worm drives, belt drives, and other actuators known in the art.

The CT scanner also includes a data channel that routes projection measurement results from the photon counting detectors and the detector unit 103 to a data acquisition system 176, a processor 170, memory 178, network controller 174. The data acquisition system 176 controls the acquisition, digitization, and routing of projection data from the detectors. The data acquisition system 176 also includes radiography control circuitry to control the rotation of the annular rotational portion 110 and 130. In one implementation data acquisition system 176 will also control the movement of the table 116, the operation of the X-ray source 112, and the operation of the X-ray detectors. The data acquisition system 176 can be a centralized system or alternatively it can be a distributed system. In an implementation, the data acquisition system 176 is integrated with the processor 170. The processor 170 performs functions including reconstructing images from the projection data, pre-reconstruction processing of the projection data, and post-reconstruction processing of the image data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back-projection, iterative image reconstruction methods, or stochastic image reconstruction methods. Both the processor 170 and the data acquisition system 176 can make use of the memory 178 to store, e.g., projection data, reconstructed images, calibration data and parameters, and computer programs.

The processor 170 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 178 can be a hard disk drive, CD-ROM drive, DVD drive, FLASH drive, RAM, ROM or any other electronic storage known in the art.

The network controller 174, such as an Intel Ethernet PRO network interface card from Intel Corporation of America, can interface between the various parts of the CT scanner. Additionally, the network controller 174 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In one implementation, the X-ray source 112 is a single source emitting a broad spectrum of X-ray energies.

The detector unit 103 can use energy-integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

FIG. 2 illustrates an inner ring topology for a CT scanner. The primary difference between the CT scanner in FIG. 1 and the CT scanner in FIG. 2 is that, in FIG. 2, the X-ray source 112 and the rotational component 110 to which the X-ray source 112 is fixed are outside the circular component 120 to which the PCDs are fixed. In one implementation, the back surface of each PCD is provided a protective rear cover to shield the PCDs from irradiation from behind as the X-ray source 112 travels outside the circular component 120 of the sparsely placed photon-counting detectors.

Both the X-ray source 112, collimator 114 (e.g., a bow-tie filter), and the detector unit 103 rotate around the object OBJ in aperture 215 while the photon-counting detectors PCD1 through PCDN are stationary with respect to the object OBJ in aperture 215. In one implementation, the X-ray source 112 and collimator 114 are mounted on the first rotational component 110 mounted in the gantry 140 so that the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, the detector unit 103 having energy-integrating detectors arranged in a third-generation geometry is mounted on the second rotational component 130 that is rotatably fixed to the gantry 140. The detector unit 103 is maintained at a position diametrically opposed position from the X-ray source 112 with the object OBJ in the intermediary space between the X-ray source 112 and the detector unit 103—the rotational components 110 and 130 rotating outside the stationary circular component 120, on which the photon-counting detectors PCD1 through PCDN are fixed in a predetermined sparse arrangement.

A Faraday cage is a box, cage, or array of electrically conductive material intended to shield its contents from electromagnetic radiation. It can be formed of any electrically conductive material, substantially transparent to X-rays and opaque to light, such as a low-Z metal sheet. The effectiveness of a Faraday cage depends on the wavelength of the radiation, the size of the mesh in the cage, the conductivity of the cage material, the thickness of the cage, and other variables.

Figure 3:
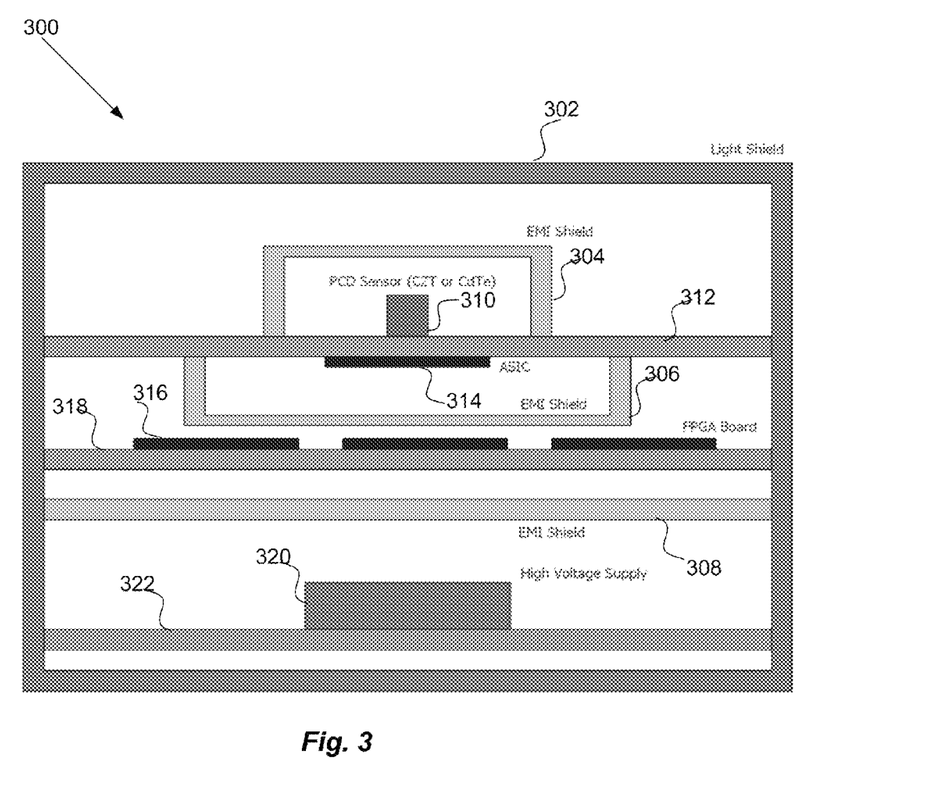
FIG. 3 illustrates an exemplary graph of a Faraday cage with a photon-counting detector system inside the Faraday cage.

As illustrated in FIG. 3, the Faraday cage 300 includes a light shield 302, a first electromagnetic (EMI) shield 304, a second EMI shield 306, and a third EMI shield 308. A PCD 310 is disposed on one side of a first substrate 312, and enclosed by the first EMI shield 304. An application-specific integrated circuit (ASIC) chip 314 is disposed on the other side of the first substrate 312, and is enclosed by the second EMI shield 306. FPGA boards 316 are disposed on a second substrate 318. The FPGA boards 316 are beneath the second EMI shield 306 and above the third EMI shield layer 308. A high-voltage supply 320 is disposed on the third substrate layer 322 and underneath the third EMI shield 308. The ASIC chip 314 and the FPGA boards 316 are configured to function as front-end readout electronics for PCDs.

In one embodiment, the signals from the PCD are collected by a readout circuit. The readout channel outputs an analog signal that is processed by a preamplifier and is then inputted into an analog-to-digital (A/D) converter. The A/D converter is clocked at a high frequency (typically 40 to 100 MHz) and outputs a digital signal. The digital signal is then transferred to the processor 170 for detecting the incident photons. Digital samples are processed by an algorithm implemented in a digital filter that determines the timestamp and an amplitude of the signal. The readout circuit continuously samples analog signals and produces large data sets to be further processed in an image processing chain.

Figure 4A:
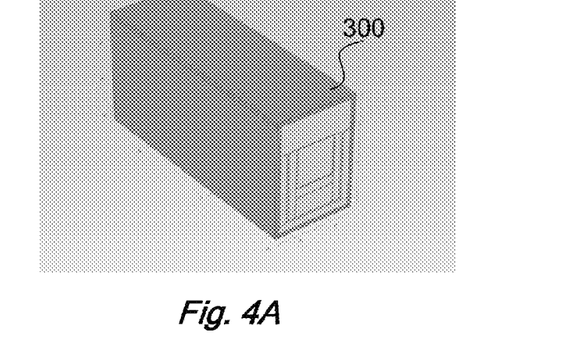
FIGS. 4A-4C illustrates an exemplary cross-section graph of the Faraday cage, the photon-counting detector and a collimator.
Figure 4B:
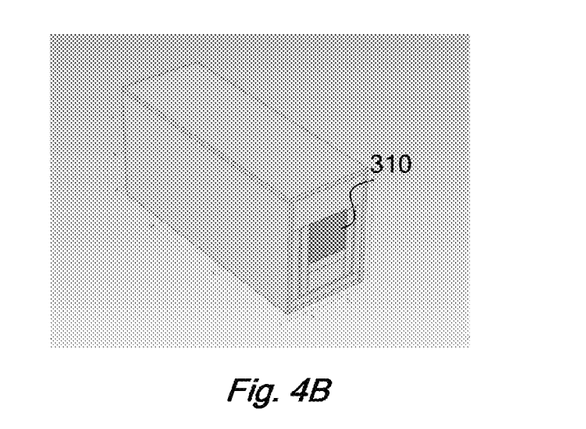
Figure 4C:
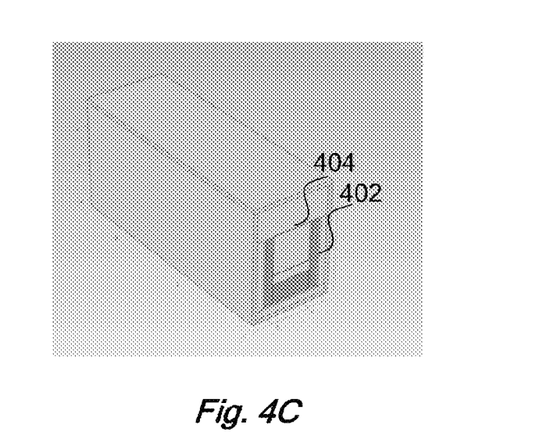

FIGS. 4A-C are perspective side-views of a Faraday cage 300, the PCD 310, and a collimator 402. FIGS. 4A-C illustrate that the Faraday cage 300 encloses the PCD 310 and the collimator 402. Further, the collimator 402 surrounds the PCD 310 except at the anode side 404 of the PCD 310. The collimator absorbs X-rays emitted from an X-ray source.

The Faraday cage 300 functions both as an electromagnetic shield and as a light shield. However, as a metallic structure, the Faraday cage 300, which is biased at a certain electrical potential, alters an operating electrical potential of the nearby PCD 310. As a result, the operating electrical potential has undesirable high- and low-electrical field regions inside the Faraday cage.

Figure 5A:
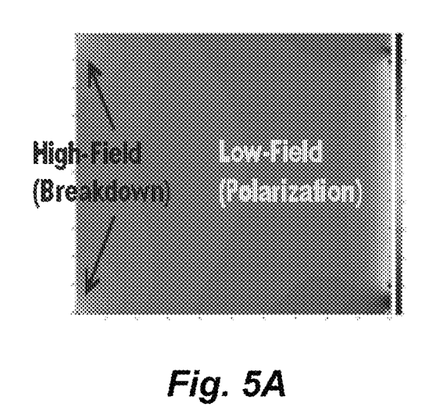
FIGS. 5A-5C illustrate exemplary operating electric fields of the photon-counting detector in the Faraday cage biased at 1000V, at −500V, and −1000V respectively.
Figure 5B:
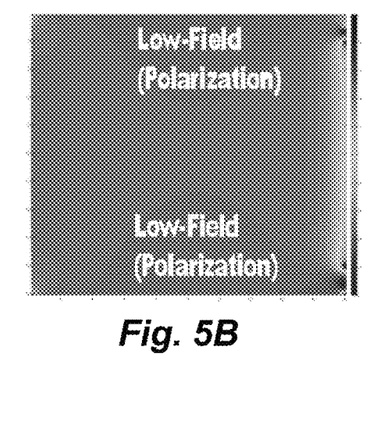
Figure 5C:
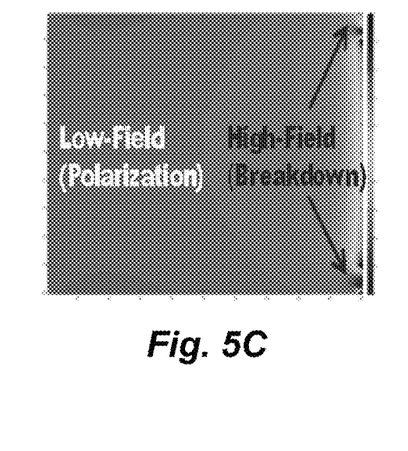

FIGS. 5A-C illustrate the operating electrical field E of the Faraday cage 300 when biased at different electrical potentials.

FIG. 5A shows the operating electrical field E of the PCD 310 in the Faraday cage 300 when biased at 0 V. High electrical fields at the left side of FIG. 5A cause breakdowns of the electrical field. Applying an electrical field that is above the breakdown voltage to the PCD 310 generates excess tunneling currents in the absorption region of the PCD 310. The tunneling currents increase the noise of the PCD 310 and thereby dramatically reduce the accuracy of the PCD 310. Low electrical fields in a middle and a left side of the graph shown in FIG. 5A reduce mobility of some of the carriers (e.g., electron or holes), and provoke polarization effects of the PCDs 310. The polarization effects reduce a field strength across the PCD 310 and decrease a charge collection efficiency. These changes generate a non-linear response of the PCD 310.

FIG. 5B shows the operating electrical field E of the PCD 310 in the Faraday cage when biased at −500 V. Compared with FIG. 5A, a low electrical field dominates the operating electrical field and generates polarization effects.

FIG. 5C shows the operating electrical field E of the PCD 310 in the Faraday cage when biased at −1000 V. Compared with FIG. 5A, the high electrical field at a right side of the graph shown in FIG. 5C causes breakdowns of electrical field, generates excessive tunneling current, and degrades the accuracy of the PCD 310. The low electric field at the left side of FIG. 5C generates polarization effects and decreases the charge collection efficiency.

Figure 6A:
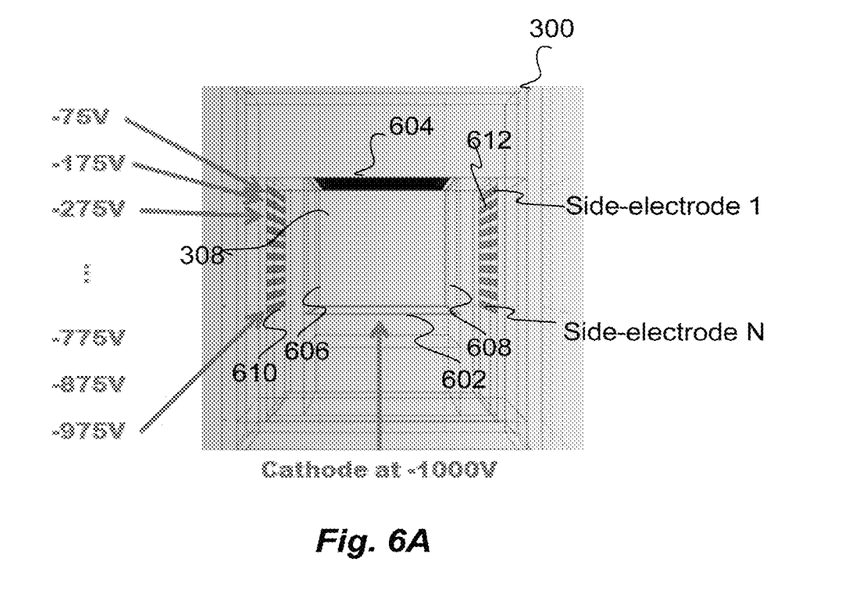
FIG. 6A illustrates an exemplary embodiment of a Faraday cage with enabled side-electrodes.

Now referring to FIG. 6A, a first embodiment of the Faraday cage 300 with side electrodes is illustrated. Inside the Faraday cage 300, a PCD 310 is formed from a semiconductor material, such as CdZnTe or CdTe. A face of the crystal has a large single-cathode electrode 602. The opposite face of the crystal is the anode side 604 and includes an array of rectangular or square anode pixels with variable size. A voltage difference is applied between the anode electrode 602 and the cathode electrode 604 so that a detector electrical field is generated. When photons are incident on the crystal, the photons generally lose all energy in the crystal as a result of ionization and leave pairs of mobile electrons and holes in a small localized region of the crystal. As a result of the detector electric field, holes drift to the cathode electrode 604 and electrons drift to the anode electrode 602. This process induces charges on anode pixels, which are sensed and processed by appropriate electronic circuits.

In this embodiment, the cathode of the PCD 310 is biased at −1000 V and the anode of the PCD is biased at 0V. In addition to the cathode face 602, the PCD 310 has two side surfaces 606 and 608 that are also surrounded by the Faraday cage 300. As shown in FIG. 6A, two groups of side-electrodes (610 and 612), which are attached to the Faraday cage 300, face the side surfaces 606 and 608 of the PCD 300, respectively. Each group of side-electrodes includes a plurality of inter-digitated electrode stripes (e.g., side-electrode 1 through side-electrode N), which are alternately arranged in parallel. The side-electrode 1 is close to the anode side 604 of the PCD 300, while the side-electrode N is close to the cathode side 602 of the PCD 300. The side-electrode strips can be thin layers of copper disposed uniformly on the side surface of the Faraday cage 300. A uniform negative bias voltage is applied over the entire group.

The side-electrodes are connected by resistors to a high-voltage power supply bus. A voltage applied to the voltage-biased side-electrodes decreases from the anode side of the PCD to the cathode side of the PCD. The high voltage bus, in turn, is connected with the power supply, which biases the bus and the side-electrode strips from −75 to −975 VDC, in one embodiment.

Figure 7A:
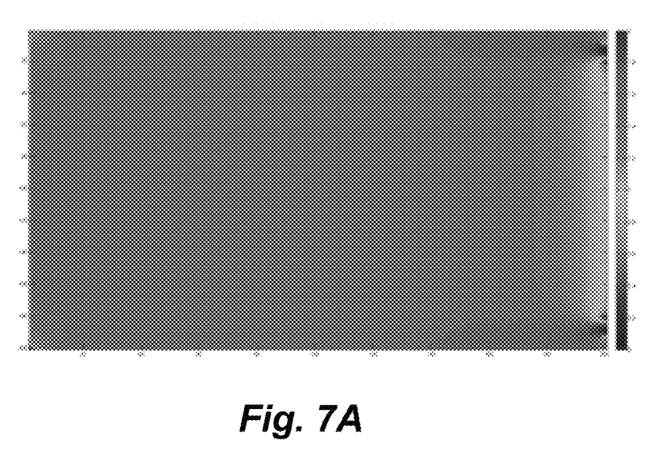
FIG. 7A and FIG. 7B illustrate exemplary operating electric fields of the photon-counting detector in the Faraday cage with the enabled side-electrodes biased at 0V and at −1000 V, respectively.
Figure 7B:
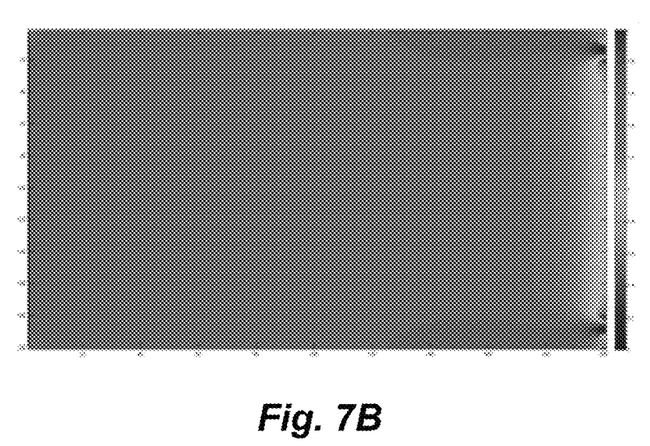

FIG. 7A and FIG. 7B illustrate operating electric fields of a PCD 310 in a side-electrode-enabled Faraday cage 300, which is biased at 0 V and at −1000 V, respectively. The side-electrodes are biased as shown in FIG. 6A. Both FIG. 7A and FIG. 7B show that the respective operating potential inside the detector is uniform and independent of the potential applied to the Faraday cage 300.

Other embodiments can be implemented by alternating numbers, relative positions, and bias voltages that are applied to the side-electrodes, by alternating materials of the Faraday cage, by alternating dielectric insulating materials between the PCD 310 and the collimator, by alternating geometries (e.g., thickness, width and height) between the PCD 310 and the collimator, by alternate dielectric insulating materials between the collimator and the Faraday cage, by alternating geometries (e.g., thickness, width, and height) between the collimator and the Faraday cage 300, and by using different biasing configurations, such as horizontal strips of side-electrodes, and single zig-zag electrodes with resistors embedded. Detailed descriptions of the different embodiment are described below.

Figure 8A:
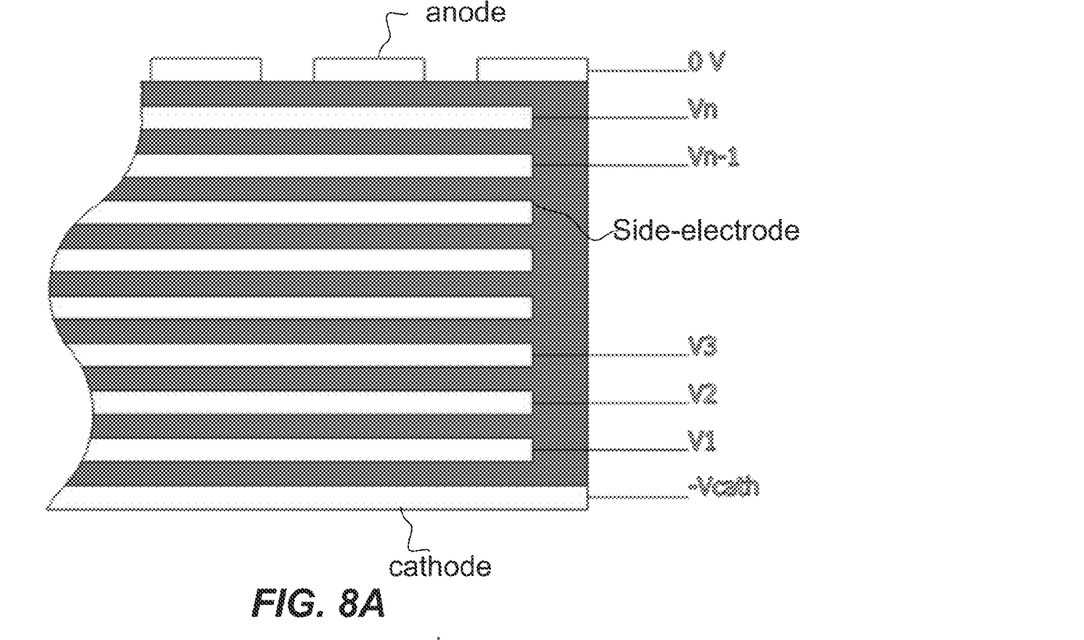
FIG. 8A and FIG. 8B illustrate side-stripes with different widths.
Figure 8B:
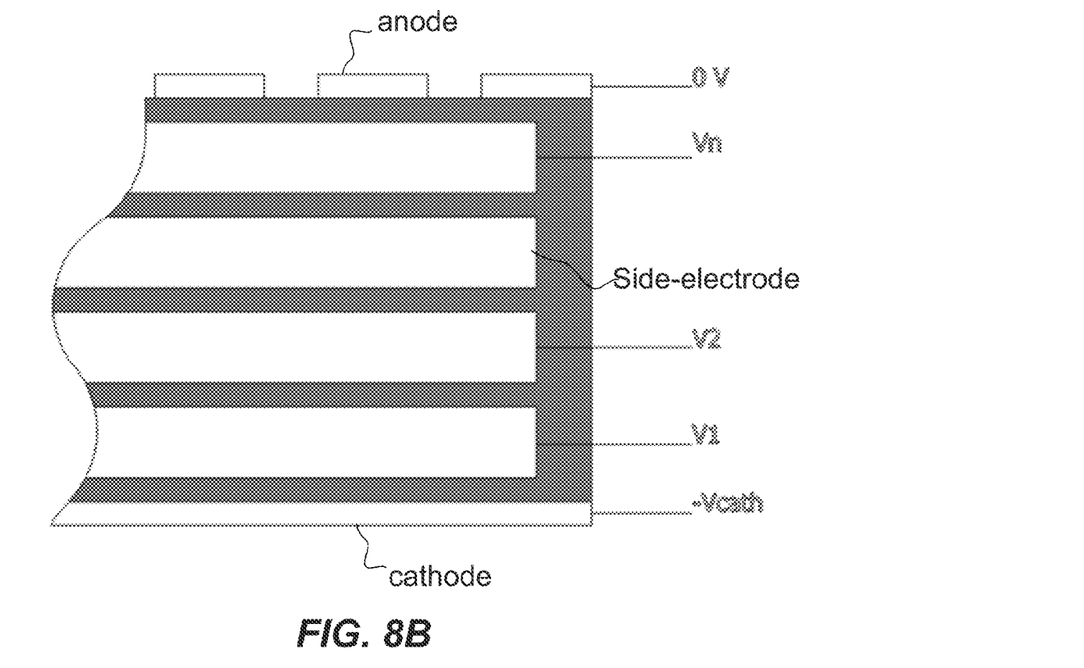

FIGS. 8A and 8B illustrate exemplary embodiments implemented by alternating the number of side-electrodes, the relative position of side-electrodes and the configuration and number of bias voltages applied to side-electrodes.

The embodiment of FIG. 8A includes a larger number of narrower side-electrodes, which enables more uniform operating field inside the PCD, compared with a smaller number of wider side-electrodes in the embodiment shown in FIG. 8B. However, the larger number of narrower side-electrodes requires a larger number of power supplies, and a more complex fabrication process compared with the smaller number of wider side-electrodes.

Figure 6B:
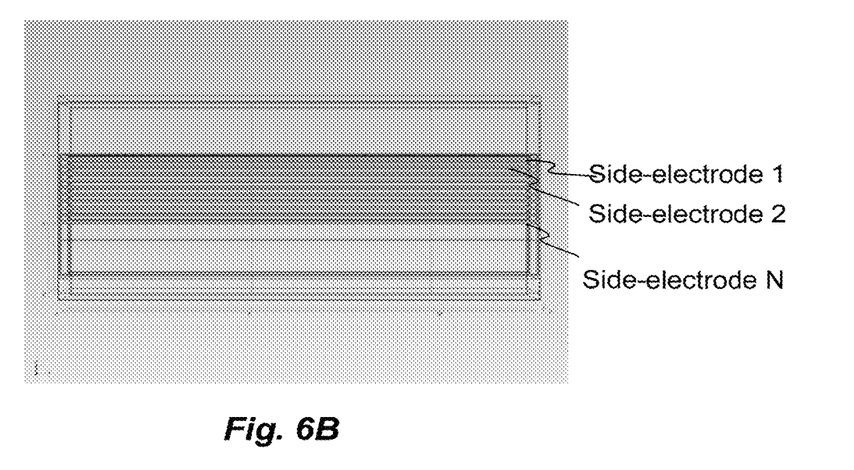
FIG. 6B illustrates an exemplary graph of the side-electrodes inside the Faraday cage.
Figure 9:
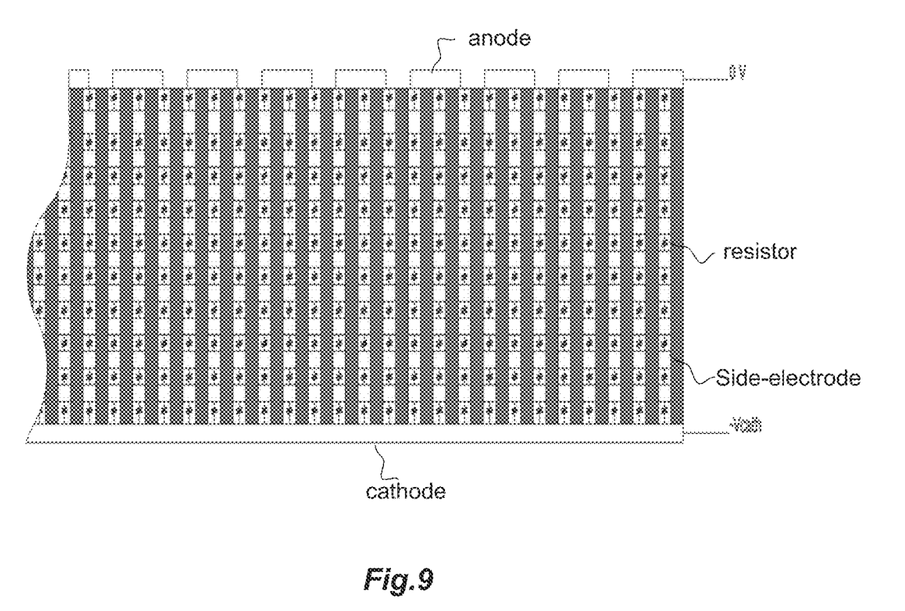
FIG. 9 illustrates vertical side-stripes with embedded resistors.

FIG. 9 illustrates another embodiment of vertical side-electrode strips. Instead of using the horizontal electrode strips parallel with the cathode and anode, as shown in FIG. 6B, vertical stripes with embedded resistors are implemented. One end of each of the vertical strips is located at an anode of the PCD, and the other end of each of the vertical strips is located at the cathode of the PCD. Therefore, these vertical stripes can use the same power supplies that are used on the anode and the cathode of the PCD.

Figure 10:
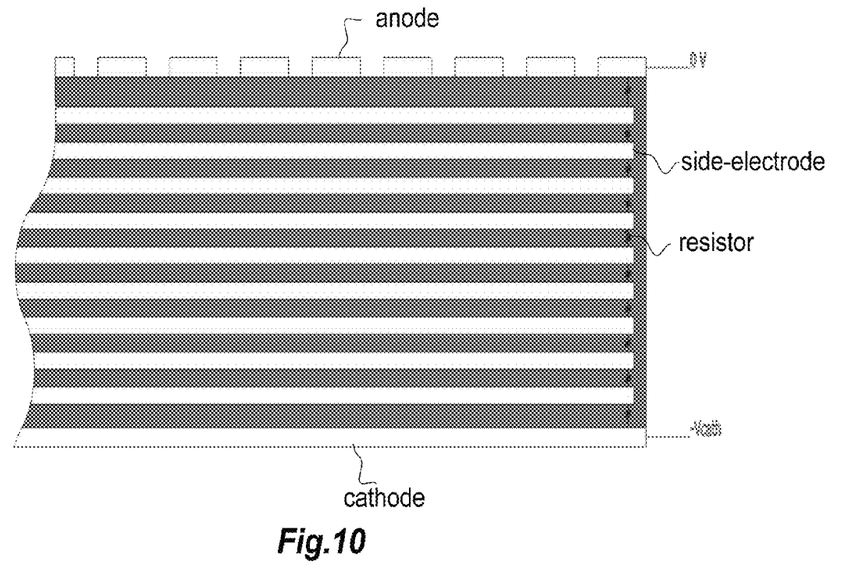
FIG. 10 illustrates horizontal strips with a vertical chain of resistors.

FIG. 10 illustrates another embodiment of electrode strips. A group of horizontal side-strips are connected together through a single vertical chain of resistors. One end of the vertical chain of resistors is the cathode, and the other end of the vertical chain of resistors is an anode. Multiple vertical chains of resistors can also be used instead of the single vertical chain of resistors. By using the single or multiple vertical chains of resistors, the electrode side-strips can use the same number of power supplies used on the PCD and exhibit a more uniform operating field.

Figure 11:
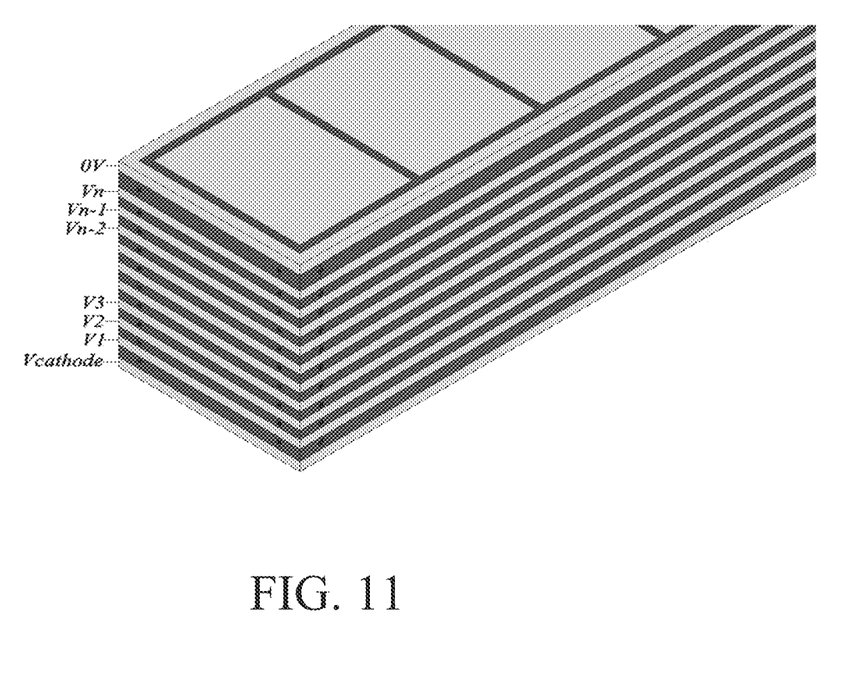
FIG. 11 illustrates an embodiment having side-electrodes on all four lateral surfaces of a detecting device.

In another alternative embodiment, the side electrodes are arranged on all four lateral surfaces of the detector, not just the two lateral surfaces in the slice direction. This embodiment is illustrated in FIG. 11.

Moreover, the number, dimensions, and position of the side-electrodes can vary with respect to the detector dimensions and technology available to manufacture them. Increasing the number of side electrodes results in a smoother and piecewise electrical potentials at the surface of the detector. Further, as described above, side-electrodes can cover all four lateral surfaces of the detector, forming a closed "loop". In one embodiment, side-electrodes can be positioned a small distance away from the lateral surface of the semiconductor radiation detector. Moreover, the embodiments described above can also be applicable to conventional third-generation CT detectors.

The above-described embodiments have several advantages over conventional detectors. For example, side-electrodes make the operating field uniform throughout the entire volume of the semiconductor. Further, side-electrodes make the operating field the highest possible, avoiding regions where the lines concentrate, which limits detector operating bias due to localized detector breakdown. Further, the disclosed embodiments facilitate the use of thinner detectors (e.g., W<2.0 mm) with larger thickness (T~3.0 mm), which improves charge-collection efficiency, maintaining a higher operating field with no charge loss at the surface.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) detector apparatus, comprising:
    a plurality of detectors, each detector being arranged inside a Faraday cage having a plurality of voltage-biased side electrodes arranged on at least one side surface of the Faraday cage.

2. The apparatus of claim 1, wherein the detectors include photon counting detectors (PCDs).

3. The apparatus of claim 1, wherein the detectors are arranged in a ring.

4. The apparatus of claim 2, wherein each PCD comprises:
    a rectangular semiconductor crystal having a first face and a second face, wherein the first face and the second face are parallel;
    a cathode side including a cathode electrode covering the first face; and
    an anode side including a plurality of anode pixels on the second face.

5. The apparatus of claim 4, wherein a voltage applied to the voltage-biased side-electrodes decreases from the anode face of the PCD to the cathode face of the PCD.

6. The apparatus of claim 4, wherein the semiconductor crystal is one of CdZnTe and CdTe.

7. The apparatus of claim 1, wherein the Faraday cage is composed of a low-Z material.

8. The apparatus of claim 2, wherein each PCD further comprises:
    a collimator; and
    a dielectric insulating material disposed between the PCD and the collimator.

9. The apparatus of claim 1, wherein the side electrodes are arranged in two groups on opposite sides of the Faraday cage and the side electrodes in each group are horizontal-strip electrodes.

10. The apparatus of claim 9, wherein the side-electrodes in each group are single resistor-embedded zig-zag electrodes.

11. The apparatus of claim 2, wherein a width of each of side-electrodes is reduced to enable a uniform operating field inside the PCD.

12. The apparatus of claim 2, wherein a single vertical chain of resistors are used to connect the side-electrodes together, a first end of the single vertical chain of resistors being connected to a cathode of the PCD, and a second end of the single vertical chain of resistors being connected to an anode of the PCD.

13. The apparatus of claim 2, wherein multiple vertical chains of resistors are used to connect the side-electrodes together, a first end of each of the multiple vertical chains of resistors being connected to a cathode of the PCD, and a second end of each of the multiple vertical chains of resistors being connected to an anode of the PCD.

14. The apparatus of claim 2, wherein the side electrodes are arranged in two groups on opposite sides of the Faraday cage and the side electrodes in each group are vertical-strip electrodes with embedded resistors, a first end of each of the side-electrodes being connected to a cathode of the PCD, and a second end of each of the side-electrodes being connected to an anode of the PCD.

15. The apparatus of claim 2, further comprising:
an X-ray source configured to emit X-rays that are received by the PCDs.

16. A computed tomography (CT) imaging apparatus, comprising:
a plurality of detectors, each detector being arranged inside a Faraday cage having a plurality of voltage-biased side electrodes arranged on at least one side surface of the Faraday cage.

17. The apparatus of claim 16, wherein the detectors include photon counting detectors (PCDs).

18. The apparatus of claim 16, wherein the side electrodes are arranged on all four side surfaces on the Faraday cage.

19. The apparatus of claim 17, wherein each PCD comprises:
a rectangular semiconductor crystal having a first face and a second face, wherein the first face and the second face are parallel;
a cathode side including a cathode electrode covering the first face; and
an anode side including a plurality of anode pixels on the second face.

20. The apparatus of claim 19, wherein a voltage applied to the voltage-biased side-electrodes decreases from the anode side of the PCD to the cathode side of the PCD.

* * * * *